(12) United States Patent
Petit

(10) Patent No.: US 9,919,412 B2
(45) Date of Patent: Mar. 20, 2018

(54) HANDLE FOR A TOOL, TOOLING SYSTEM AND TOOLS FOR SUCH A SYSTEM

(71) Applicant: SAFE ORTHOPAEDICS, Eragny sur Oise (FR)

(72) Inventor: Dominique Petit, Verton (FR)

(73) Assignee: SAFE ORTHOPAEDICS, Eragny sur Oise (FR)

( * ) Notice: Subject to any disclaimer, the term of this patent is extended or adjusted under 35 U.S.C. 154(b) by 423 days.

(21) Appl. No.: 14/402,460

(22) PCT Filed: May 28, 2013

(86) PCT No.: PCT/FR2013/051184
§ 371 (c)(1),
(2) Date: Mar. 9, 2015

(87) PCT Pub. No.: WO2013/178934
PCT Pub. Date: Dec. 5, 2013

(65) Prior Publication Data
US 2015/0174754 A1 Jun. 25, 2015

(30) Foreign Application Priority Data
May 28, 2012 (FR) ..................................... 12 54897

(51) Int. Cl.
*B25G 1/06* (2006.01)
*A61B 17/70* (2006.01)
(Continued)

(52) U.S. Cl.
CPC ............ *B25G 1/06* (2013.01); *A61B 17/7082* (2013.01); *B25G 1/08* (2013.01); *A61B 17/8875* (2013.01);
(Continued)

(58) Field of Classification Search
CPC ........ B25G 1/06; B25G 1/08; A61B 17/7082; A61B 17/8875; A61B 17/0046; A61B 17/00464; A61B 17/00477
(Continued)

(56) References Cited

U.S. PATENT DOCUMENTS 1,463,077 A * 7/1923 Gandell ................. B25G 1/043
81/177.2
1,511,738 A * 10/1924 Lownsbery ............ B25G 1/043
16/429
(Continued)

FOREIGN PATENT DOCUMENTS

EP 1563963 A1 8/2005
GB 635391 A 4/1950

*Primary Examiner* — Hadi Shakeri
(74) *Attorney, Agent, or Firm* — Bachman & LaPointe, P.C.

(57) ABSTRACT

A handle for actuating a removable instrument formed by a rod extended by an active area, said rod extending in a longitudinal direction OX, said rod having at least one means for mechanically coupling with said handle, characterized in that said handle has a transverse insertion slot, symmetrical relative to a plane YOZ, wherein the axis OY is perpendicular to the longitudinal axis OX, said slot opening onto a surface of the handle and having a section corresponding to the section of the coupling area of said rod, in order to allow said coupling area to be inserted by way of a movement in a direction OY, until it butts against the bottom of said slot, said bottom extending in a plane parallel to the plane XOZ, wherein XOZ designates a plane perpendicular to the axis OY.

10 Claims, 4 Drawing Sheets

(51) Int. Cl.
*B25G 1/08* (2006.01)
*A61B 17/88* (2006.01)
*A61B 17/00* (2006.01)

(52) U.S. Cl.
CPC ............... *A61B 2017/0046* (2013.01); *A61B 2017/00464* (2013.01); *A61B 2017/00477* (2013.01)

(58) Field of Classification Search
USPC .............................................. 81/180.1, 177.2
See application file for complete search history.

(56) References Cited

U.S. PATENT DOCUMENTS

| | | | | |
|---|---|---|---|---|
| 2,518,755 | A * | 8/1950 | Clarke | B25G 1/005 408/240 |
| 5,525,000 | A * | 6/1996 | Belobraydich | G09F 7/18 40/610 |
| 5,741,289 | A | 4/1998 | Jolly et al. | |
| 5,832,794 | A * | 11/1998 | Fowler | B25B 13/08 81/177.2 |
| 7,971,914 | B1 | 7/2011 | Pladson | |
| 2005/0279193 | A1 * | 12/2005 | Darby | B25G 1/043 81/177.2 |
| 2010/0229693 | A1 | 9/2010 | Chen | |

\* cited by examiner

HANDLE FOR A TOOL, TOOLING SYSTEM AND TOOLS FOR SUCH A SYSTEM

BACKGROUND

The present invention relates to the field of surgical instruments for spinal stabilisation operations using bone-anchor elements such as screws, an intersomatic cage, or any other spinal implants by a posterior, anterior or posterolateral approach.

The invention relates specifically to an instrument kit according to the invention intended mainly, but not exclusively for lumbar, thoracic or even cervical spinal osteosynthesis surgery, by minimally invasive or open surgical approaches.

The surgical procedure requires a great variety of instruments for screwing, tamponading, percussion, curettage, etc. These instruments have a rod extended by a working area.

In order to simplify the instruments, it is possible to use a single handle, configured to allow the adaptation of interchangeable instruments.

The invention is not, however, limited to the field of surgery, and relates more generally to tool-holder handles that allow the adaptation of a plurality of interchangeable tools.

PRIOR ART

Tool-holding handles that enable the insertion of interchangeable tools are known in the prior art, such as screwdrivers having a cavity opening out at a front opening, the cavity having a non-circular shape to prevent the rotation of the tool relative to the handle about the longitudinal axis. A locking ring provides the blocking of the tool inserted in the cavity by a clamping system or by a bayonet fitting.

DRAWBACKS OF THE PRIOR ART

Said handles are well adapted to tools intended for exerting a rotation torque in a longitudinal direction only. However, they are not provided for tools intended for transmitting multiaxial forces, for example in the form of percussion, optionally accompanied by a simultaneous rotation movement, or lever forces in any direction.

SUMMARY

In order to solve the drawbacks of the prior art, the present invention proposes a handle for actuating a removable instrument formed by a rod extended by an active area, said rod extending in a longitudinal direction OX, said rod having at least one means for mechanically coupling with said handle, characterised in that said handle has a transverse insertion slot, symmetrical relative to a plane YOZ, wherein the axis OY is perpendicular to the longitudinal axis OX, said slot opening onto a surface of the handle and having a section corresponding to the section of the coupling area of said rod, in order to allow said coupling area to be inserted by way of a movement in a direction OY, until it butts against the bottom of said slot, said bottom extending in a plane parallel to the plane XOZ, wherein XOZ designates a plane perpendicular to the axis OY, the depth of said slot being greater than half the thickness of the handle, said handle also having, on either side of said slot, according to the axis OX, two cavities opening respectively onto either one of the parallel edges of the mid-plane YOX, one of said cavities opening out at the front surface of the handle, said cavities being configured such as to allow the insertion of said rod by a rotation relative to the axis OZ of the coupling area after insertion into said slot, and to block said rotation when the rod reaches a position parallel to the longitudinal axis OX.

Said solution makes it possible to insert the active area of the rod in the slot opening onto a side surface of the handle, in a position in which the rod forms an angle relative to the longitudinal axis, and then to tilt the rod such as to bring same into a working position according to the longitudinal axis, in which the position thereof is then locked. Said embodiment makes it possible to produce a very solid handle, making it possible to transmit multiaxial stresses and forces, both by percussion and by rotation.

Unlike the solutions of the prior art, the movements that occur when placing the tool take place in directions and movements which differ from those to which the tool is subjected during the use thereof. This prevents the appearance of play and wear in the mechanism for inserting and replacing the tool.

According to a first alternative embodiment, the handle comprises a ferrule extending the area opening out at one of the cavities, said ferrule being movable between a position in which the slot thereof is placed aligned with the lateral opening of the cavity closest to the opening surface such as to allow the passage of the rod during the pivoting movement relative to the axis OZ, and a position in which said ferrule prevents the pivoting of said rod about an axis OZ.

According to a second alternative embodiment, the handle comprises an abutment movable between a position in which it allows the passage of the rod during the pivoting movement relative to the axis OZ, and a position in which it prevents the pivoting of said rod according to the axis OZ.

Advantageously, the handle according to the invention comprises a projection erected according to an axis OZ perpendicular to said supporting bottom of said slot, in order to guide the pivoting of the coupling area of the rod in the plane XOY.

According to a specific alternative embodiment, the axis OY is perpendicular to the axis OX.

According to a preferred embodiment, at least one of said cavities has at least one projecting shoulder engaging with a matching projecting area provided on the coupling area of the rod when the rod is positioned longitudinally according to the axis OX. The presence of one or more shoulders arranged in at least one of the cavities of the handle and one or more matching projecting areas supported by the coupling area of the rod makes it possible to block the axial translation of the rod relative to the handle.

Preferably, at least one of said projections is formed by an arched shoulder.

The invention also relates to a tooling system made up of at least one removable instrument and a handle that conforms with the aforementioned handles.

Advantageously, said removable instrument has two active areas arranged at the ends of the rod, the rod having at least one area for coupling with the handle. Such an instrument makes it possible to provide two different types of functions, by simple reversal of the mounting in the handle.

The invention further relates to an accessory instrument of an aforementioned handle, characterised by having a rod extended at each end thereof by an active area arranged on either side of at least one coupling area, the rod also having at least one area for coupling with the handle, said coupling area having a means for pivoting about a matching means provided in the bottom of the insertion slot of said handle.

Advantageously, the coupling area of the rod has a flattened section. Thus, when positioned in the handle, i.e. assembled with the handle such as to extend in the longitudinal direction OX, the rotation of the rod on the handle about the axis OX is blocked.

BRIEF DESCRIPTION OF THE DRAWINGS

Further objectives and advantages of the invention will become apparent from the following description made in reference to the appended drawings, wherein.

DETAILED DESCRIPTION

Figure 1:
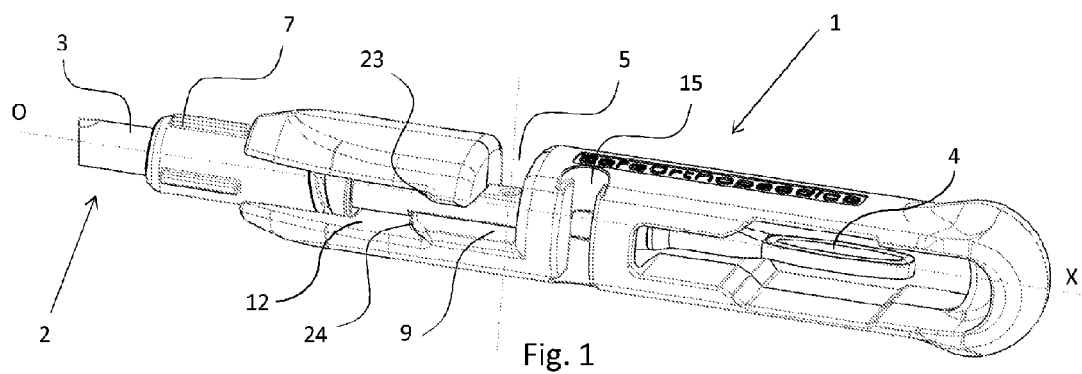
FIG. 1 is a perspective view of a handle according to the invention, with an instrument inserted in the handle.

FIG. 1 is an overview of a handle (1) provided with an instrument (2). Said instrument (2) is made up of a cylindrical rod (3), with a round section in the described example. Each end of the cylindrical rod has an active area (4) adapted for a specific job: screwdriver cross or blade, spatula, polygonal section for tightening a plug or a screwable part, etc.

The handle (1) in the described example is made up of a moulded fibreglass-filled plastic part. It can also be made by machining or casting a metal alloy or any other material.

Specifically, the handle (1) comprises a tubular body extending in a longitudinal axis OX and having a transverse slot (5) extending in a direction OY. In the described example, the direction OY is perpendicular to the longitudinal direction OX, but can also form an angle other than 90° relative to the longitudinal direction, in order to have a skewed slot. The opening of said slot (5) corresponds to the section of the coupling area (6) of the rod (3) of the instrument (2).

The instrument (2) can thus be inserted in the handle (1) when positioned in the direction OY, and inserted by moving in a direction OZ, in the plane YOZ. The axis OZ is perpendicular to the plane XOY.

The instrument (2) is then tilted by pivoting about the axis OZ, in order to come into the longitudinal position OX in which it is shown in FIG. 1.

The handle (1) has a ferrule (7) at the front which makes it possible to lock the instrument (2) when it is inserted in the handle.

Figure 2:
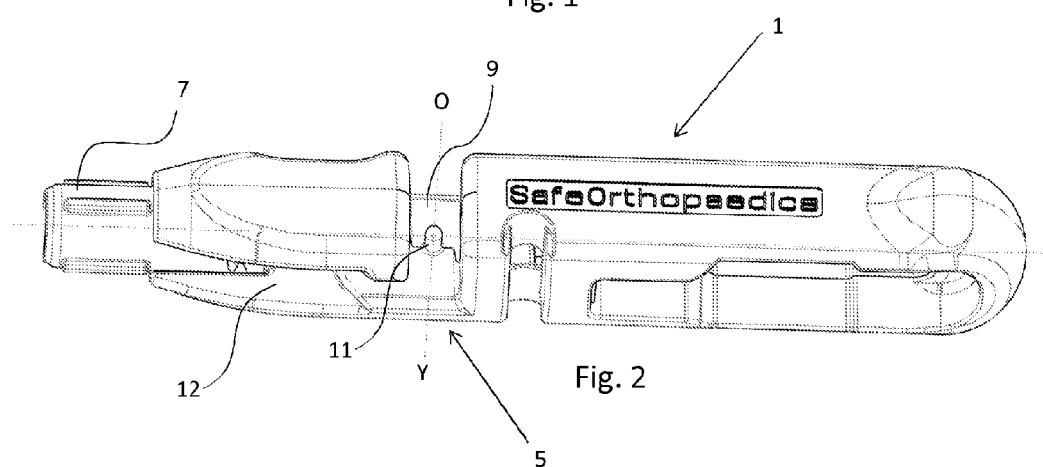
FIG. 2 is a perspective view of a handle according to the invention, with no instrument inserted in the handle.

FIG. 2 shows a handle without an instrument. The slot (5) has a flat bottom (9) on which the coupling area (6) of the instrument rests, which advantageously has a flattened section (10) of the coupling area (6) of the instrument. The presence of the flattened section (10) of the coupling area (6) makes it possible to block the rotational movement of the rod about the axis OX when the latter arrives in the longitudinal position in the handle, i.e. when the rod is assembled with the handle such as to lie in the longitudinal direction OX.

The flat bottom (9) extends parallel to the plane XOY. It has a lug (11) standing in a direction OZ perpendicular to the bottom (9). The coupling area (6) of the instrument has a matching cavity (19) suitable for guiding the pivoting of the rod in the plane XOY, around said lug (11). Other configurations can be provided: for example, a hemispherical boss projecting relative to the bottom of the slot (5), or even a cylindrical or hemispheric cavity provided in the bottom of the slot, such as to receive a matching projection provided on the active area (6) of the instrument.

Figure 3:
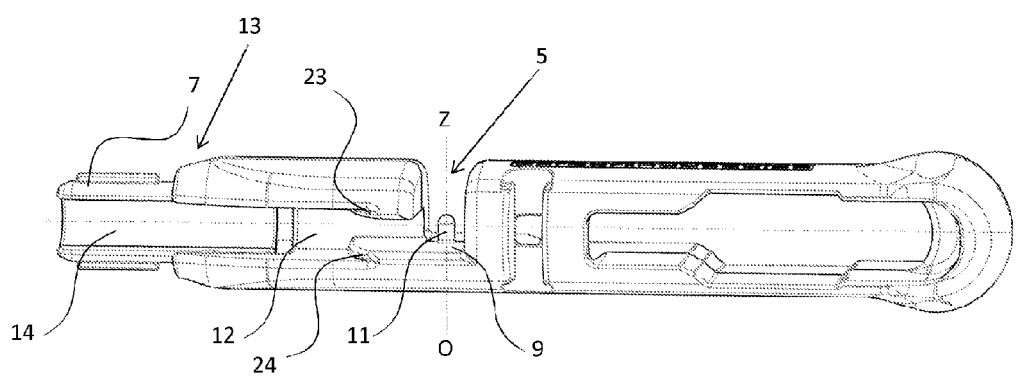
FIG. 3 is a view of the handle after a longitudinal rotation by a quarter-turn relative to the view shown in FIG. 2.

FIG. 3 corresponds to a quarter-turn rotation of the handle relative to the position depicted in FIG. 2. In the plane YOZ, one of the surfaces of the handle has a front longitudinal slot (12) extending from the transverse slot (5) until the front end (13) of the handle. Said front slot (12) opens out onto the front end of the handle and is extended by the lateral opening (14) of the ferrule (7). The section of the front slot (12) corresponds to the section of the rod of the instrument.

The body of the handle also has a second transverse slot (15) making it possible to position the rod of an instrument in order to exert, for example, a twisting force.

Figure 4:
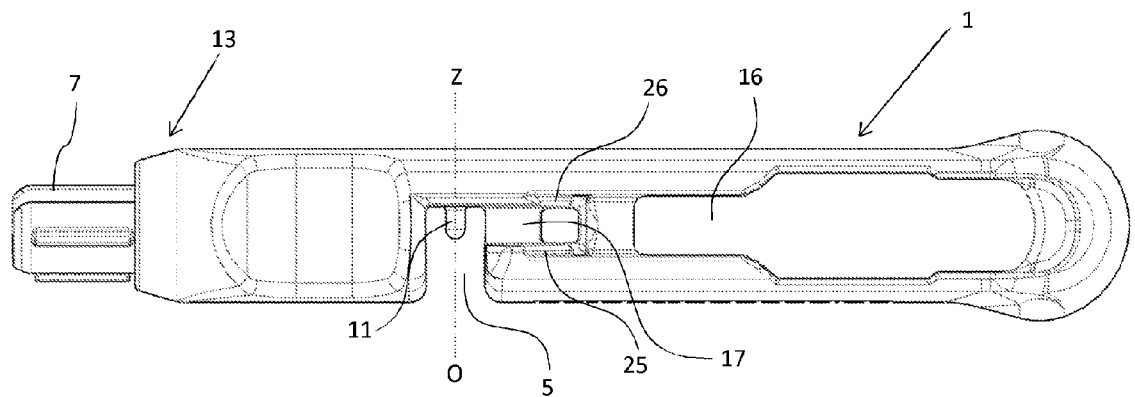
FIG. 4 is a view of the handle after a longitudinal rotation by a half-turn relative to the view shown in FIG. 3.
Figure 4:
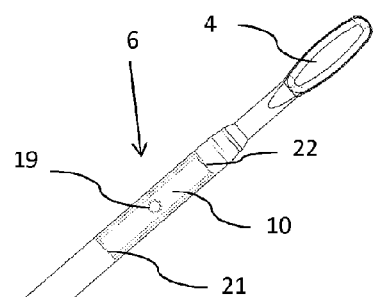

On the opposite surface shown by FIG. 4, the handle has a rear longitudinal slot (16) extending from the transverse slot (5) over a length greater than the length of the instrument comprised between the coupling area and the end of the working area.

Said rear slot (16) has at least one abutment limiting the movement of the rod of the instrument, said abutment being made up of the bottom (17) of the rear slot (16) in the described example.

Figure 5:
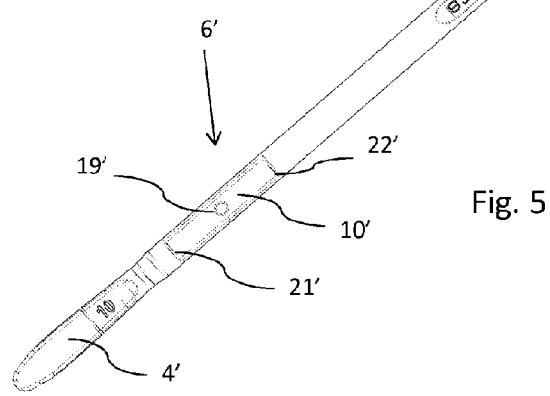
FIG. 5 is a view of an instrument that can be adapted to such a handle.

FIG. 5 is a view of an example of a reversible instrument for such a handle. It has a cylindrical rod (3) extended at either end thereof by an active area (4, 4'). At the rear of each of the active areas (4, 4'), the rod has a coupling area (6, 6') made up, on either side of the longitudinal mid-plane of the rod, by a flattened section (10, 10') with a length corresponding to the width of the transverse slot (5) of the handle (1).

The edges (21, 22; 21', 22') of the instrument (2) form shoulders that match the arched shoulders (23, 24, 25, 26) provided in the longitudinal slots (12, 16).

When the rod (3) is in place in the handle (1), the edges (21, 22; 21', 22') of the coupling area (6, 6'), the arched shoulders (23, 24, 25, 26) and the longitudinal slots (12, 16) block the relative movements between the rod (3) and the handle (1), in the longitudinal direction, and the transmission of longitudinal forces exerted on the handle (1) until the active area (4, 4'), for example during a use for percussion.

Figure 6:
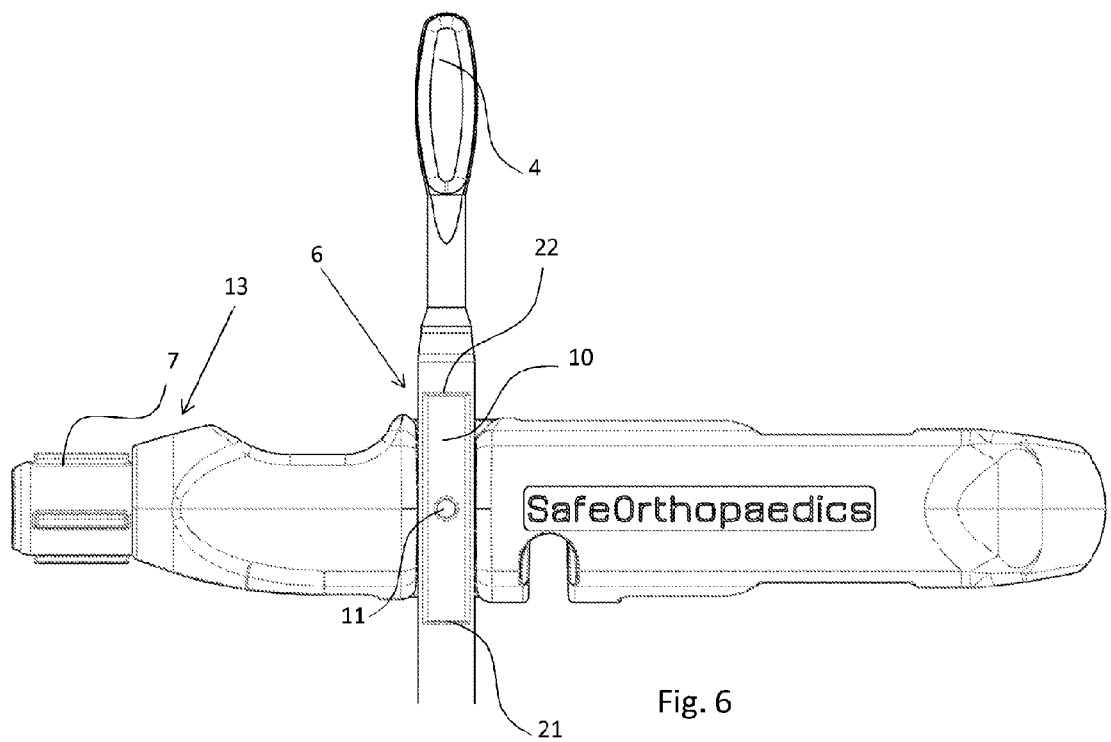
FIGS. 6 to 8 are views in a direction OZ with three consecutive stages of insertion of the instrument in the handle.
Figure 7:
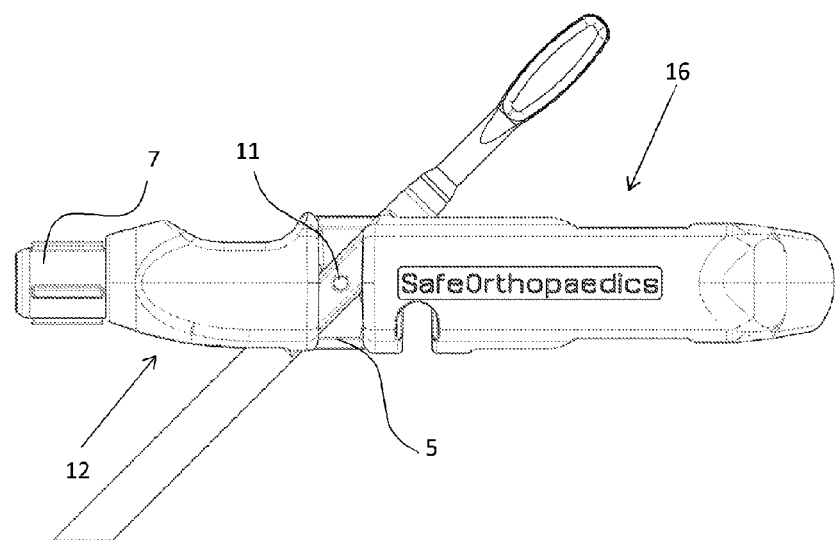
Figure 8:
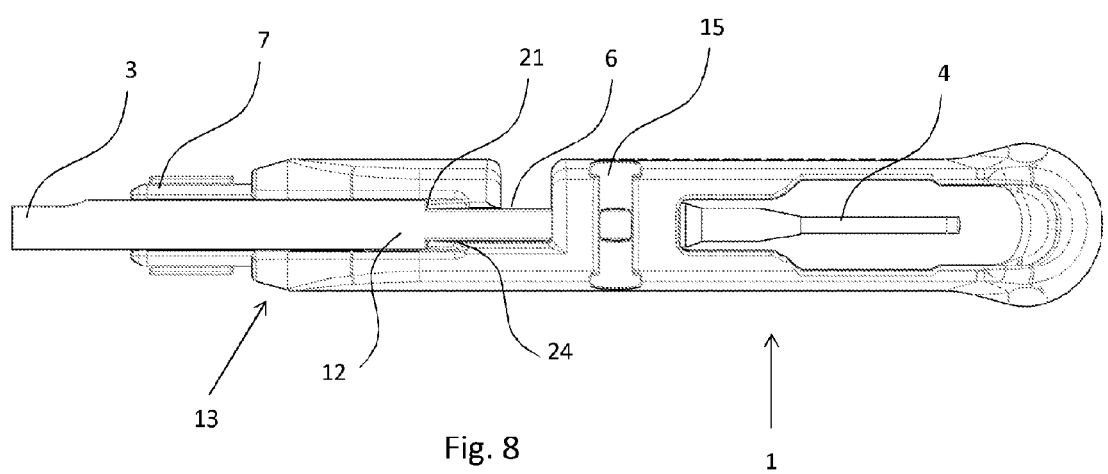

FIGS. 6 to 8 show the various steps of inserting an instrument into the handle.

The process starts by positioning the coupling area (6, 6') in the slot (5) by pushing the rod to the bottom of said transverse slot (5) (FIG. 6). Care is taken to place the coupling area (6, 6') in the slot (5) such that the lug (11) arranged on the bottom of the slot (5) is housed in the matching cavity (19) provided for said purpose in the coupling area of the rod.

Next, the instrument is pivoted about the lug (11), in the plane XOY, in order to insert the rod in the front (12) and rear longitudinal slots (16) (FIG. 7) until reaching a position parallel to the longitudinal axis OX, the pivoting of the rod being halted by the longitudinal wall placed opposite the front longitudinal slot (12).

When the rod has tilted into longitudinal position, it is immobilised by a rotation of the ferrule (7). The arched shoulders (21, 22; 21', 22') of the instrument (2) engage with the matching shoulders (23, 24, 25, 26) provided in the longitudinal slots (12, 16) of the handle (1) (FIG. 8, before pivoting the ferrule), thus blocking all axial movements of the rod in the handle. Furthermore, due to the presence of the flattened section (10), the rotation movement of the rod about the longitudinal axis OX is prevented.

The invention claimed is:

1. A handle for actuating a removable instrument formed by a rod extended by an active area, said rod extending in a longitudinal direction OX, said rod having at least one coupling area for mechanically coupling with said handle, said handle has a transverse insertion slot, symmetrical relative to a plane XOZ, wherein an axis OZ is perpendicular to the longitudinal axis OX, said transverse insertion slot opening onto a surface of the handle and having a section corresponding to a section of the coupling area of said rod, in order to allow said at least one coupling area to be inserted by way of a movement in a direction OZ, until it butts against a bottom of said transverse insertion slot, said bottom extending in a plane parallel to the plane XOY, wherein XOY designates a plane perpendicular to the axis OZ, said bottom having one of a projection or a matching cavity to corporate with one of a matching cavity or a projection on said at least one coupling area, respectively, a depth of said insertion slot being greater than half a thickness of the handle, said handle also having, on either side of said insertion slot, according to the axis OX, two cavities opening respectively onto either one of parallel edges of the plane ZOX, one of said cavities opening out at a front surface of the handle, said cavities being configured such as to allow the insertion of said rod by a rotation relative to the axis OZ of the coupling area after insertion into said insertion slot, the rotation being guided by said projection and said matching hole, at least one of said cavities has at least one arched shoulder engaging with a projection area provided on the coupling area of the rod when the rod is positioned longitudinally according to the axis OX, configured to block further rotation when the rod reaches a position parallel to the longitudinal axis OX.

2. The handle according to claim 1, further comprising a ferrule extending an area opening out at one of the cavities, said ferrule being movable between a position in which a slot thereof is placed aligned with a lateral opening of the cavity closest to a connecting surface such as to allow the passage of the rod during the rotating movement about the axis OZ, and a position in which said ferrule prevents the pivoting of said rod about the axis OZ.

3. The handle according to claim 1, wherein the projection is erected according to the axis OZ perpendicular to said bottom of said insertion slot, guiding the rotation of the coupling area of the rod in the plane XOY.

4. The handle according to claim 1, wherein the axis OY is perpendicular to the axis OX.

5. The handle according to claim 1, in combination with an accessory instrument comprising a rod extended at either end thereof by an active area arranged on either side of at least one area for mechanically coupling with the handle, each of the coupling area having one of a matching cavity or a projection for pivoting about a corresponding projection or a matching cavity provided in the bottom of the insertion slot of said handle.

6. The instrument according to claim 5, wherein the coupling area of the rod has a flattened section.

7. A tooling system made up of a removable instrument formed by a rod extended by at least one active area, said rod extending in a longitudinal direction OX and having at least one coupling area for mechanically coupling with a handle, and a handle for actuating the removable instrument, said handle has a transverse insertion slot, symmetrical relative to a plane XOZ, wherein an axis OZ is perpendicular to the longitudinal axis OX, said insertion slot opening onto a surface of the handle and having a section corresponding to a section of the coupling area of said rod, in order to allow said coupling area to be inserted by way of a movement in a direction OZ, until it butts against the a bottom of said insertion slot, said bottom extending in a plane parallel to the plane XOY, wherein XOY designates a plane perpendicular to the axis OZ, one of said bottom or the coupling area having a projection with the other one having a matching hole, a depth of said insertion slot being greater than half a thickness of the handle, said handle also having, on either side of said insertion slot, according to the axis OX, two cavities opening respectively onto either one of parallel edges of the plane ZOX, one of said cavities opening out at the front surface of the handle, said cavities being configured such as to allow the insertion of rod by a rotation relative to the axis OZ of the coupling area after insertion into said insertion slot, the rotation being guided by said projection and said matching hole, at least one of said cavities has at least one arched shoulder engaging with a projection area provided on the coupling area of the rod when the rod is positioned longitudinally according to the axis OX, configured to block further rotation when the rod reaches a position parallel to the longitudinal axis OX.

8. The tooling system according to claim 7, wherein said removable instrument has an active area arranged on either side of the coupling area, the rod also having at least one area for coupling with the handle.

9. A handle for actuating a removable instrument formed by a rod extended by an active area, said rod extending in a longitudinal direction OX, said rod having at least one area for mechanically coupling with said handle, said handle has a transverse insertion slot, symmetrical relative to a plane XOZ, wherein an axis OZ is perpendicular to the longitudinal axis OX, said transverse insertion slot opening onto a surface of the handle and having a section corresponding to a section of the coupling area of said rod, in order to allow said coupling area to be inserted by way of a movement in a direction OZ, until it butts against a bottom of said transverse slot, said bottom extending in a plane parallel to the plane XOY, wherein XOY designates a plane perpendicular to the axis OZ, a depth of said slot being greater than half a thickness of the handle, said handle also having, on either side of said slot, according to the axis OX, two cavities opening respectively onto either one of parallel edges of the plane ZOX, one of said cavities opening out at a front surface of the handle, said cavities being configured such as to allow the insertion of said rod by a rotation relative to the axis OZ of the coupling area after insertion into said slot, at least one of said cavities has at least one arched shoulder engaging with a projection area provided on the coupling area of the rod when the rod is positioned longitudinally according to the axis OX, configured to block further rotation when the rod reaches a position parallel to the longitudinal axis OX and a ferrule extending an area opening out at one of the cavities, said ferrule being movable between a position in which a slot thereof is placed aligned with a lateral opening of the cavity closest to a connecting surface such as to allow the passage of the rod during the pivoting movement about an axis OZ, and a position in which said ferrule prevents the pivoting of said rod about the axis OZ.

10. A tooling system made up of a removable instrument formed by a rod extended by at least one active area, said rod extending in a longitudinal direction OX and having at least one means for mechanically coupling with a handle, and a handle for actuating the removable instrument, said handle has a transverse insertion slot, symmetrical relative to a plane XOZ, wherein an axis OZ is perpendicular to the longitudinal axis OX, said slot opening onto a surface of the handle and having a section corresponding to a section of the coupling area of said rod, in order to allow said coupling area to be inserted by way of a movement in a direction OZ, until it butts against a bottom of said slot, said bottom extending in a plane parallel to the plane XOY, wherein XOY designates a plane perpendicular to the axis OZ, the depth of said slot being greater than half the thickness of the handle, said handle also having, on either side of said slot, according to the axis OX, two cavities opening respectively onto either one of parallel edges of the plane ZOX, one of said cavities opening out at the front surface of the handle, said cavities being configured such as to allow the insertion of rod by a rotation relative to the axis OZ of the coupling area after insertion into said slot, and to block further rotation when the rod reaches a position parallel to the longitudinal axis OX, and a ferrule extending an area opening out at one of the cavities, said ferrule being movable between a position in which a slot thereof is placed aligned with a lateral opening of the cavity closest to a connecting surface such as to allow the passage of the rod during the pivoting movement about an axis OZ, and a position in which said ferrule prevents the pivoting of said rod about the axis OZ.

* * * * *